US006352700B1

(12) United States Patent
Luu et al.

(10) Patent No.: US 6,352,700 B1
(45) Date of Patent: *Mar. 5, 2002

(54) LOTIONIZED TISSUE PRODUCTS CONTAINING A PH BALANCE COMPOUND FOR THE SKIN

(75) Inventors: Phuong V. Luu; T. Philips Oriaran, both of Appleton; David W. White, Neenah; Anthony O. Awofeso, Appleton; Gary L. Schroeder, Neenah; Richard E. Fredricks, Appleton, all of WI (US)

(73) Assignee: Fort James Corporation, Deerfield, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/303,660

(22) Filed: May 3, 1999

(51) Int. Cl.[7] .................. A01N 25/34; A01N 25/24
(52) U.S. Cl. ............... 424/402; 424/404; 424/407; 514/846; 514/847; 514/887
(58) Field of Search ................. 424/402, 404, 424/407; 514/846, 847, 887

(56) References Cited

U.S. PATENT DOCUMENTS

| 3,955,586 | A | * | 5/1976 | Hartsough | 132/7 |
| 3,982,017 | A | * | 9/1976 | Thiele | 424/318 |
| 4,234,464 | A | * | 11/1980 | Morshauser | 252/544 |
| 4,362,781 | A | * | 12/1982 | Anderson | 428/291 |
| 4,772,501 | A | * | 9/1988 | Johnson et al. | 428/74 |
| 4,775,678 | A | * | 10/1988 | Su et al. | 514/396 |
| 4,941,995 | A | * | 7/1990 | Richards | 252/407 |
| 5,629,081 | A | * | 5/1997 | Richards et al. | 442/96 |
| 5,871,763 | A | * | 2/1999 | Luu et al. | 424/402 |

* cited by examiner

Primary Examiner—Thurman K. Page
Assistant Examiner—S. Tran
(74) Attorney, Agent, or Firm—Nixon Peabody LLP

(57) ABSTRACT

A substrate treated with a lotion including a skin pH balancing compound and a base lotion. The pH balancing compound is preferably an organic acid, such as an alpha-hydroxy acid, an alpha-dihydroxy acid, or a beta-hydroxyacid, a combination of an organic acid and a salt of an organic acid, or a buffer combination, such as combinations of citric acid and disodium phosphate, or disodium citrate and sodium hydroxide. The preferred lotion has the effect of maintaining the skin acid mantle while making the treated substrate, preferably tissue, towel or napkin, optionally wet-strengthened, wipe or nonwoven material, feel smooth, lubricious and nongreasy. The skin care benefits of the lotionized substrate are expressed whether the product is used dry or prewetted with water.

38 Claims, No Drawings

LOTIONIZED TISSUE PRODUCTS CONTAINING A PH BALANCE COMPOUND FOR THE SKIN

BACKGROUND OF THE INVENTION

This invention relates to lotionized tissue and towel products which minimize irritation and redness and other deleterious effects common to the repeated use of such products on the skin.

Absorbent tissue and towel products, such as facial tissue, bath tissue and paper towels, wipes and nonwoven materials have been used to absorb body fluids and cleanse and dry the skin. It has long been recognized, however, that products such as these tend to abrade and dry-out the skin causing uncomfortable irritation and redness. For example, there are numerous pre-moistened wipe products which can be found in the marketplace. However, many of these contain volatile alcohol solutions which remove skin lipids and fats, causing dryness.

To reduce these deleterious effects, tissue products, e.g., tissue and towel products, wipes and nonwoven materials, have been provided with a variety of lotions and lubricant formulations enabling the products to better glide across the surface of the skin, and/or deposit lotions on the surface of the skin in an attempt to replenish lost natural skin oils. However, there exists in the art a need for products which more effectively address the drawbacks. While numerous products containing lubricants or lotions exist in the marketplace which attempt to address those problems, this invention is believed to constitute an advancement over those.

For example, lotionized facial tissue such as Puffs Plus and Kleenex® ColdCare™ with Lotion, are examples of commercial products which claim to be comforting and soothing to the skin due to their lotion formulas. The lotion can transfer to the skin in use. However, the facial tissue products are mostly used to wipe and remove nasal discharges, and inadequately address the problem as irritation, and red and inflamed skin on the nose as well as its surrounding skin in the upper lip area, still result upon repeated use.

Charming® Plus is an example of a commercial bathroom tissue containing lotion, which claims enhanced cleansing of the skin and reduced irritation and inflammation. The reduction in irritation and inflammation is achieved from the lubricity of the lotion. Again, however, improvement is needed.

It is an object of the invention, therefore, to provide improved absorbent tissue and towel products, such as facial tissue, bath tissue and paper towels, wipes and non-woven materials, such that skin irritation, inflamation and other adverse effects are reduced.

SUMMARY OF THE INVENTION

The invention, therefore, is directed to tissue and towel products, as well as other paper products such as wipes and non-woven materials, which minimize irritation and redness and other deleterious effects common to the repeated use of such products on the skin. A lotion which maintains the skin pH balance and provides a smooth, lubricious, non-greasy feeling layer on the skin, is transferred to the skin. More particularly, the invention relates to a tissue product treated with a lotion capable of maintaining skin pH balance comprising a skin pH balancing compound and a nongrease-feelng base lotion preferably containing an emollient and a retention/release agent as base ingredients. The base lotion has the effect of making the treated tissue product feel nongreasy and lubricious. Skin care benefits of the lotionized tissue product are expressed whether the product is used dry or prewetted with water.

We have discovered that existing lotionized tissue products are limited in their inability to maintain the pH balance of the skin. This, in turn, leads either directly, or indirectly to the various drawbacks attributable to their repeated use.

The human skin is divided into two basic layers, the dermis and the epidermis. The dermis is the deeper layer and is largely structural. The outermost layer next to the dermis, the epidermis, is comprised of four layers: stratum basal, stratum spinosum, stratum granulosum, and the top exposed surface, the stratum corneum. The stratum corneum (SC) is composed of layers of non-viable flat cells, each about 0.5 $\mu$m thick and about 30 to 40 $\mu$m long, with SC thickness ranging from about 6 to 15 $\mu$m. This layer of tightly bound cells is recognized as the body's principal barrier of defense against invasion of microorganisms, and the entry of topically applied substances into the body.

In 1928, Schade and Marchionini reported the existence of skin acidity and the importance of this mantle in preventing infection. They referred to the skin surface (SC) as an "acid mantle" having a protective role and preventing growth of many environmental bacteria and fungi. Today the factors regulating skin surface pH are still unknown. However, there is sufficient evidence to support the barrier function and self-disinfection of the skin's "acid mantle". The pH value of human "acid mantle" is generally ranges from 4 to 6. On the other hand, the body's internal pH is about neutral, ranging from about 7.35 to about 7.46. Skin pH varies among different body areas and also depends on the skin moisture—skin areas with higher moisture having a higher pH.

Any cleansing method with soap, solvent or even using tap water (having a pH of about 8) tends to increase the pH of stratum corneum. For example, simply washing with an alkaline soap alone raises the skin pH, and the time required to return to normal skin pH value is between 30 minutes, for normal skin, and many hours for people with intolerance to soap.

Various reports have shown that skin alkalinization has negative effects, such as irritant dermatitis and optopic skin disease. Infant skin pH for the two weeks after birth is close to neutral. For this reason, the newborn skin's ability to control growth of microorganisms is low and may have low resistance to infection. Other reports have claimed that an increase in skin pH is an important contributing factor in diaper dermatitis. A recent study correlated skin pH with the severity of experimentally induced irritant dermatitis. It has been found that high skin pH coincides with high transepidermal water loss, which is one of the more sensitive parameters used to quantify an irritant response in the skin.

While products exist that are said to address the problems of skin irritation and inflamation, they inevitably fail to address the short term impact of various additives on the pH balance of the skin, i.e., the skin's acid mantle. To put this into perspective, one need only to consider conventional facial tissue, toilet tissue, napkin and paper towel products that are used for wiping dry or wet skin. Upon contact with skin, the tissue products transfer some of the chemicals present in the tissue to the skin surface. These additives may be detrimental to maintaining the skin's "acid mantle." For example, a tissue product containing baking soda (a highly alkaline compound) is produced by KC/Scott (Kleenex®

Cottonelle® Baking Soda—Advanced Personnel Hygiene). The transfer to the user's skin of such a highly alkaline compound is entirely inconsistent with maintaining the skin's acid mantle.

Thus, in accordance with one aspect of the present invention, there is provided a lubricious, nongreasy-feeling lotionized tissue, wipe or nonwoven material, whereby the lotion transfers to the skin during use to provide a breathable, smooth layer which acts to maintain the skin acid mantle and the proper skin moisture/vapor balance and which users find soothing to irritated or damaged skin, and which users may find soothing to irritated skin and which may facilitate healing of chapped skin and skin suffering from discomfort, such as diaper rash or hemorrhoids. Preferably, the skin pH balancing compound is an organic acid, a combination of an organic acid and the salt of an organic acid, or a buffer combination.

In accordance with another aspect of the present invention, there is provided a product treated with a lotion which, optionally, contains one or more of the following: a surfactant which aids in skin cleansing, and a medicinal agent, such as an antimicrobial agent which kills bacteria and fungi commonly found on skin, thereby providing an enhanced cleansing and deodorizing benefit.

In accordance with a further aspect of the invention, there is provided a tissue, towel or napkin, optionally wet-strengthened, or wipe or nonwoven material, such as that used for diaper, incontinence and menstrual pad coverstock, that is treated with a lotion comprising at least one compound capable of maintaining the skin pH balance and a nongreasy-feeling base lotion.

In accordance with a still further aspect of the present invention, there is provided an embossed tissue, embossed towel, or embossed napkin, optionally wet-strengthened, that is treated with a lotion comprising at least one compound capable of maintaining the skin pH balance and a nongreasy-feeling base lotion.

In accordance with yet another aspect of the present invention, there is provided a lubricious, nongreasy-feeling lotionized tissue, wipe or nonwoven material, whereby the lotion forms a cold cream when contacted with water and transfers to the skin during use to provide a breathable, smooth layer which acts to maintain the skin acid mantle and the proper skin moisture/vapor balance and which users find soothing to irritated or damaged skin.

DETAILED DESCRIPTION OF PREFERRED EMBODIMENTS

The term "lotion" as used herein when referring to the lotion of the invention, is defined as a combination of at least one skin pH balancing compound and a base lotion. All percentages, ratios and proportions used herein are by weight of the base lotion, unless otherwise specified. The temperature of human skin is between about 30° C. and about 37° C. and room temperature is between about 20° C. and about 25° C.

The preferred embodiments will be described herein in terms of lotionized tissue products. However, as noted above the invention equally encompasses other absorbent and non-absorbent, woven and non-woven applicators, lotionized according to the invention.

A preferred embodiment of the invention thus provides a lotionized tissue product capable of maintaining the skin's acid mantle. The acid mantle of skin is maintained by incorporating into a base lotion at least one pH balancing compound. This pH balancing compound is mixed with a base lotion before application of the lotion to the tissue product. When skin is contacted with the lotionized tissue product, the pH balancing compound transfers to the skin and maintains the acid mantle of the skin. While not wishing to be bound by any theory, one possible mechanism for maintaining the acid mantle of skin upon contacting the skin with the lotionized tissue product of the invention, includes the formation of a breathable water vapor barrier film on the skin, which maintains the skin pH between 4 and 6.

The lotion's capacity to balance the skin's pH can reduce skin irritation and inflammation for people with normal skin or sensitive skin. Achieving a balance with the skin's pH also has other advantages which include: (1) enhancing the skin's barrier function against microbial and fungal infections for better cleansing and protection; (2) retarding the odor generated by bacteria which grow on proteins in perspiration at pH>6; and (3) neutralizing the alkaline substances, such as those present in nose discharges and the by-products of urine and fecal matter (the pH of urine and feces is about 4.6 to 8.4).

The tissue product can be prepared according to conventional processes (including TAD, CWP and variants thereof) known to those skilled in the art. The tissue product may be creped or uncreped. For example, conventional wet pressed tissues are typically prepared by first preparing and mixing the fibrous raw material in a vat. The stock is transferred usually at a consistency of about 1% to about 5% through a centrifugal pump to a headbox, where the consistency is about 0.1% to about 1.0%. The fibrous mixture is deposited into a moving foraminous wire such as fourdrinier wire to form a web mat. Water is drained through this wire by use of vacuum and drainage elements. The embryonic web is transferred onto a hot Yankee dryer via one or two press rolls. The web is about 25% to about 50% solids after passing through the press rolls. The transferred web is adhered onto the surface of the Yankee which has been previously prepared by spraying an adhesive material directly onto the metal surface. The dried web is then removed via the use of a creping doctor which scrapes off the web from the surface of the Yankee dryer metal drum. The dried Web is then wound up at the reel of the paper machine. The lotionized tissue can be obtained by applying the lotion including the pH balancing compound to the substrate according to conventional application methods known to those skilled in the art.

In one embodiment, the pH balancing compound for the lotion is an organic acid. Preferred organic acids include alpha-hydroxy acids, alpha-dihydroxy acids, and beta-hydroxy acids. Specific examples of suitable organic acids include glycolic acid, alpha-acetyl glycolic acid, lactic acid, tartaric acid, alpha-acetyl lactic acid, alpha-hydroxy isobutyric acid, salicylic acid, mandelic acid, ortho-acetyl mandelic acid, benzilic acid, ortho-acetyl benzilic acid, malic acid, citric acid, gluconic acid, pyruvic acid, sorbic acid, etc.

The pH balancing compound may also be a combination of an organic acid and a salt of organic acid. Also, the pH balancing compound may be a buffer combination, such as buffer combinations comprising citric acid and disodium phosphate, and buffer combinations comprising disodium citrate and sodium hydroxide.

According to one embodiment of the invention, the pH balancing compound is mixed with a variety of base lotions suitable for the preparation of lotionized tissue products. In a preferred embodiment of the invention, thee balancing compound is mixed with a non-greasy feeling base lotion, such as the lotion described in U.S. Pat. No. 5,871,763 issued Feb. 16, 1999, the contents of which are incorporated herein by reference in their entirety.

The lotion may contain an emollient and/or retention/release agent, surfactant(s), medicinal agent(s) such as antimicrobial agent(s), fragrance(s), humectant(s) as well as optional components typically present in lotions of this type.

In general, the base lotion formulation should possess desired physical attributes, such as having a smooth, lubricious, nongreasy feel; the ability to at least partially transfer from the tissue product to the skin, aided by body heat or by activation with water; the ability to form a breathable layer which acts to maintain proper skin moisture/vapor balance; the ability to moisturize the skin; the ability when melted to wet the surface of the tissue product; the capability to be retained on a tissue product at about room temperature; and the ability to at least partially melt to transfer to the surface of the skin when contact is made with body heat. After transfer, at least a portion of the lotion may resolidify on the skin to form a smooth surface layer that is perceived as nongreasy.

Most preferably, the lotion is substantially free of water, i.e., anhydrous. Preferably, water is not intentionally added to the lotion. However, minor amounts of water may be present due to ambient humidity or small amounts added with optional additives.

If the pH balancing compound is an organic acid alone, the base lotion of the present invention contains preferably about 0 to 15% water, most preferably about 5% or less water. If the pH balancing compound is to be a mixture of an organic acid and a salt of an organic acid, or salt of an organic acid alone, or a buffer combination, the base lotion of the present invention preferably contains about 10 to 20% water, most preferably about 10 to 15% water.

As noted above, a product according to the present invention can be any suitable applicator that the lotion can be retained upon. Suitable applicators include a web, gauze, cotton swab, transdermal patch, container or holder. The lotion may be retained on the tissue product in any desired amount.

Preferred products include any suitable applicator web, including a flushable or nonflushable web of cellulosic fibers; a web of synthetic fibrous material; tissue, towel or napkin, optionally wet-strengthened; wipe or nonwoven material, such as that used for diaper, incontinence and menstrual pad coverstock; and the like. Suitable synthetic fibrous material includes meltblown polyethylene, polypropylene, copolymers of polyethylene and polypropylene, bicomponent fibers including polyethylene or polypropylene, and the like. The tissue product also may be embossed.

For example, a flushable or nonflushable web of cellulosic fibers can be treated with a lotion according to the invention on at least one side thereof, preferably in an amount of from about 0.1% to about 25%, more preferably from about 0.5% to about 20%, by weight of the dried fiber web with the lotion of the present invention. The web also may be of synthetic fibrous material treated on at least one side thereof, preferably in an amount of from about 0.1% to about 25%, more preferably from about 0.5% to about 20%, by weight of the dried web.

The substrate web optionally includes a wet strength agent. By a wet strength agent we mean temporary and/or permanent wet strength agents. Examples include glyoxal; glutaraldehyde; uncharged chemical moieties selected from a group consisting of dialdehydes, aldehyde-containing polyols, uncharged aldehyde-containing polymers, and cyclic ureas and mixtures thereof; aldehyde-containing cationic starch; glyoxalated polyacrylamide; latex emulsions; polyamide-epichlorohydrin; polyamine-epichlorohydrin; urea-formaldehyde; melamine-formaldehyde; polyethyleneimine; mixtures of polyvinyl alcohol and salts of multivalent anions; or mixtures thereof.

The substrate preferably exhibits an initial normalized cross direction (CD) wet tensile strength of at least about 25 grams/inch as measured using the Finch Cup method for an 18.5 lb/3000 sq. ft. ream, and a Wet Abrasion Resistance Number of at least about 4. See U.S. patent application Ser. No. 08/847,409, filed Apr. 24, 1997, the contents of which are incorporated herein by reference in their entirety.

The invention will be further illustrated with reference to the following specific examples. It is understood that these examples are given by way of illustration and are not meant to limit the disclosure or the claims.

EXAMPLES 1–5

The lotion formulations compiled in Table 1 comprise a base lotion with and without a pH balancing compound. Examples 1 and 2 relate to a lotion without a pH balancing compound, and are included in Table 1 for comparison. Examples 3–5 relate to lotions obtained by adding a pH balancing compound to a base lotion according to the invention.

The lotions in Examples 3–5 were prepared according to the following procedure: the base lotion ingredients, i.e., emollient(s), release and retention agent and surfactants were mixed together and heated to 75° C. until the mixture was completely melted. The mixture was maintained at 75° C. for about 15 minutes with moderate agitation. The pH balancing compound was then added, using high agitation, until the compound was completely melted and blended. At this point the lotion was ready for application to the tissue product.

The lotions prepared in Examples 3 to 5 according to the present invention contain a pH balancing compound (alpha-hydroxy acid). The pH value for each lotion was determined by emulsifying 0.276 g of solid lotion (equivalent to the lotion amount contained in 5 sheets of 15% lotionized tissue) in 20 ml tap water (pH=8.65) at 23° C. The emulsion was shaken for 5 minutes before measuring pH using a standard calibrated pH meter.

TABLE 1

| Chemicals | Example 1 (%) | Example 2 (%) | Example 3 (%) | Example 4 (%) | Example 5 (%) |
| --- | --- | --- | --- | --- | --- |
| Finsolv TN-C12-C15 alkyl benzoate | 30 | 35 | 35 | 30 | 30 |
| Crodacol CS 50 (Cetearyl alcohol) | 57 | 65 | 63 | 56 | 55 |
| Glucate SS (methyl glucose sesqui-stearate) | 3 | 0 | 0 | 3 | 3 |
| Glucamate SSE-20 (PEG-20 methyl glucose | 10 | 0 | 0 | 10 | 10 |

TABLE 1-continued

| Chemicals | Example 1 (%) | Example 2 (%) | Example 3 (%) | Example 4 (%) | Example 5 (%) |
|---|---|---|---|---|---|
| sesqui-stearate) | | | | | |
| Glycolic acid | 0 | 0 | 2 | 1 | 0 |
| Lactic acid | 0 | 0 | 0 | 0 | 2 |
| pH | 7.8 | 7.2 | 4.6 | 4.9 | 5.3 |

EXAMPLE 6

Example 6 provides a comparison of a lotionized tissue product containing a pH balancing compound in accordance with the present invention with other treated tissues. The lotionized tissue product was prepared by using the lotion formula described in Example 3. The lotion was applied on one-ply tissue (containing temporary wet strength agent) on a converting line. The results in Table 2 show that the invention (lotionized tissue with pH balancing glycolic acid) is the only tissue having pH balanced to skin pH. The pH of wetted tissue was determined by saturating 5 sheets of each product with 20 ml of tap water (pH=8.63). After 5 minutes, water in the tissue was removed by filtration, then measured for pH using a calibrated standard pH meter.

TABLE 2

| # | REFERENCES | pH of water extract |
|---|---|---|
| 1 | City water | 8.6 |
| 2 | Quilted Northern Bath Tissue ® | 6.7 |
| 3 | Quilted Northern Bath Tissue ®-Ultra | 6.8 |
| 4 | Charmin ® Ultra | 7.2 |
| 5 | Charmin ® Plus (with lotion) | 6.4 |
| 6 | Puffs Plus (Facial tissue with lotion) | 6.4 |
| 7 | Kleenex ® ColdCare ™ with Menthol (facial tissue) | 6.6 |
| 8 | Kleenex ® ColdCare ™ with Lotion (facial tissue) | 6.7 |
| 9 | Kleenex ® Cottonelle ® Hypo-allergenic | 7.2 |
| 10 | Kleenex ® Cottonelle ® Baking Soda (Advanced Personal Hygiene) | 7.9 |
| 11 | Lotionized tissue without pH balancing compound (Example 2) | 6.0 |
| 12 | Lotionized tissue with pH balancing glycolic acid (Example 3) | 5.2 |

Although the invention has been described above in terms of preferred embodiments, it is to be understood that variations and modifications may be resorted to as will be apparent to those skilled in the art. Such variations and modifications are to be considered within the purview and scope of the claims appended hereto. For example, preferred embodiments of the invention were described primarily in terms of a lotionized tissue product. However, the invention is applicable to other lotionized applicators capable of transferring a lotion to skin upon contact therewith.

What is claimed is:

1. A substrate treated with a lotion capable of maintaining skin pH balance comprising a skin pH balancing compound in an amount effective for maintaining the acid mantle of skin and a base lotion comprising, by weight of the lotion composition, (a) at least about 5% of an aromatic ester emollient or a fatty alcohol ester of a non-fatty organic acid emollient or mixture thereof and (b) from about 25% to about 95% of a retention/release agent, wherein said base lotion is at least partially solid at about room temperature and at least partially liquid at about human skin temperature.

2. A method of maintaining the acid mantle of skin comprising contacting the skin with a substrate, said substrate containing a skin pH balancing compound in an amount effective for maintaining the acid mantle of skin.

3. A method according to claim 2, wherein said substrate has been treated with a lotion capable of maintaining skin pH balance, said lotion consisting essentially of said skin pH balancing compound and a base lotion.

4. A method according to claim 3, wherein said pH balancing compound consists essentially of an organic acid.

5. A method according to claim 4, herein said skin pH balancing compound further consists essentially of a salt of an organic acid.

6. A method according to claim 3, wherein said skin pH balancing compound is a buffer combination.

7. A method according to claim 3, wherein said base lotion comprises, by weight of the lotion composition, (a) at least about 5% of an aromatic ester emollient or a fatty alcohol ester of a non-fatty organic acid emollient or mixture thereof and (b) from about 25% to about 95% of a retention/release agent, wherein said base lotion is at least partially solid at about room temperature and at least partially liquid at about human skin temperature.

8. A substrate treated with an anhydrous lotion that comprises a base lotion and a skin pH balancing compound comprising an organic acid in an amount effective for maintaining the acid mantle of skin.

9. A substrate treated with a lotion consisting essentially of a base lotion and a skin pH balancing compound in an amount effective for maintaining the acid mantle of skin, wherein said base lotion is capable of at least partially transferring from the substrate to the skin upon contact.

10. The substrate according to claim 9, wherein said base lotion further consists essentially of from about 0% to about 15% water.

11. The substrate according to claim 9, wherein said base lotion further consists essentially of from about 10% to about 20% water.

12. The substrate according to claim 9, wherein said base lotion further consists essentially of from about 10% to about 15% water.

13. The substrate according to claim 9, wherein said base lotion further consists essentially of less than about 20% water.

14. The substrate according to claim 9, wherein said base lotion further consists essentially of less than about 5% water.

15. The substrate according to claim 9, wherein said base lotion is anhydrous.

16. The substrate according to claim 9, wherein said amount effective for maintaining the acid mantle of skin is 1% by weight of the base lotion.

17. The substrate according to claim 9, wherein said amount effective for maintaining the acid mantle of the skin is 2% by weight of the base lotion.

18. The substrate according to claim 9, wherein said amount effective for maintaining the acid mantle of the skin is from 1% to 2% by weight of the base lotion.

19. The substrate according to claim 9, wherein said pH balancing compound consists essentially of an organic acid.

20. The substrate according to claim 19, wherein said organic acid is alpha-hydroxy acid, alpha-dihydroxy acid, beta-hydroxy acid, or combinations thereof.

21. The substrate according to claim 19, wherein said organic acid is glycolic acid, alpha-acetyl glycolic acid, lactic acid, tartaric acid, alpha-acetyl lactic acid, alpha-hydroxy isobutyric acid, salicyclic acid, mandelic acid, ortho-acetyl mandelic acid, benzilic acid, ortho-acetyl benzilic acid, malic acid, citric acid, gluconic acid, pyruvic acid, sorbic acid, or combinations thereof.

22. The substrate according to claim 9, wherein said pH balancing compound consists essentially of an organic acid and the salt of an organic acid.

23. The substrate according to claim 9, wherein said pH balancing compound is a buffer combination consisting essentially of an organic acid.

24. The substrate according to claim 23, wherein said buffer combination consists essentially of citric acid and disodium phosphate.

25. The substrate according to claim 23, wherein said buffer combination consists essentially of disodium citrate and sodium hydroxide.

26. The substrate according to claim 9, wherein said substrate is treated with said base lotion in an amount of from about 0.1% to about 25% by weight.

27. The substrate according to claim 9, wherein said substrate is treated with said base lotion in an amount of from about 0.5% to about 20% by weight.

28. The substrate according to claim 9, wherein said transfer is capable of being activated by body heat.

29. The substrate according to claim 9, wherein said transfer is capable of being activated by the addition of water.

30. The substrate according to claim 9, wherein said base lotion is capable of wetting the surface of the substrate when melted, being retained on the substrate at room temperature, and partially melting to transfer to the surface of skin when contact is made with body heat.

31. The substrate according to claim 9, wherein said base lotion further consists essentially of an emollient and a retention/release agent.

32. The substrate according to claim 9, wherein said base lotion further consists essentially of a surfactant.

33. The substrate according to claim 9, wherein said substrate is a tissue, towel, napkin, wipe, nonwoven material, diaper, incontinence product, menstrual pad coverstock, applicator, web, gauze, cotton swab, transdermal patch, container or holder.

34. The substrate according to claim 9, wherein said web is a flushable or nonflushable web of cellulosic fibers treated with an amount of said base lotion of from about 0.1% to about 25% by weight of the dry web.

35. The substrate according to claim 34, wherein said web has an initial normalized cross direction wet tensile strength of at least about 25 grams/inch as measured using the Finch Cup method and a Wet Abrasion Resistance Number of at least about 4.

36. The substrate according to claim 34, wherein said web further consists essentially of a wet strength agent.

37. The substrate according to claim 36, wherein said wet strength agent is glyoxal; glutaraldehyde; uncharged chemical moieties selected from a group consisting of dialdehydes, aldehyde-containing polyols, uncharged aldehyde-containing polymers, and cyclic ureas and mixtures thereof; aldehyde containing cationic starch; glyoxalated polyacrylamide, latex emulsions; polyamide-epichlorohydrin; polyamine-epichlorohydrin; urea-formaldehyde; melamine-formaldehyde; polyethyleneimine; mixtures of polyvinyl alcohol and salts of multivalent anions; or combinations thereof.

38. The substrate according to claim 9, wherein said web is a synthetic fibrous material treated with an amount of said base lotion of from about 0.1% to about 25% by weight of the dry web.

* * * * *